(12) United States Patent
Tyndorf et al.

(10) Patent No.: US 7,854,896 B2
(45) Date of Patent: Dec. 21, 2010

(54) CLOSED SYSTEM STORAGE PLATES

(75) Inventors: Tadeusz A. Tyndorf, Manalapan, NJ (US); Richard Cannataro, West Paterson, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 429 days.

(21) Appl. No.: 10/241,121

(22) Filed: Sep. 11, 2002

(65) Prior Publication Data

US 2003/0077207 A1    Apr. 24, 2003

Related U.S. Application Data

(60) Provisional application No. 60/324,815, filed on Sep. 25, 2001.

(51) Int. Cl.
*B01L 3/00*    (2006.01)

(52) U.S. Cl. .................................... 422/102; 435/305.3

(58) Field of Classification Search ................ 422/102, 422/104; 435/305.3, 305.1, 305.2, 305.4, 435/288.4

See application file for complete search history.

(56) References Cited

U.S. PATENT DOCUMENTS

| | | | |
|---|---|---|---|
| 3,888,770 A * | 6/1975 | Avital et al. .................. 210/238 |
| 3,978,859 A | 9/1976 | Goodenough et al. | |
| 4,204,606 A | 5/1980 | Micheli | |
| 4,542,833 A | 9/1985 | DeVaughn | |
| 4,632,673 A | 12/1986 | Tiitola et al. | |
| 5,224,515 A | 7/1993 | Foster et al. | |
| 5,247,015 A | 9/1993 | Bayan | |
| 5,288,466 A | 2/1994 | Burns | |
| 5,306,270 A | 4/1994 | Macartney et al. | |
| 5,384,096 A | 1/1995 | Burns | |
| D357,985 S | 5/1995 | Burns | |
| 5,458,854 A | 10/1995 | Burns | |
| 5,516,490 A * | 5/1996 | Sanadi ....................... 422/101 |
| 5,632,396 A | 5/1997 | Burns | |
| 5,738,233 A | 4/1998 | Burns | |
| 5,779,074 A | 7/1998 | Burns | |
| 6,106,783 A * | 8/2000 | Gamble ...................... 422/102 |
| 6,258,325 B1 | 7/2001 | Sanadi | |
| 6,436,351 B1 * | 8/2002 | Gubernator et al. ......... 422/102 |
| 2002/0054833 A1 * | 5/2002 | Qu et al. ..................... 422/102 |
| 2002/0141904 A1 * | 10/2002 | Rosen et al. ................ 422/102 |
| 2003/0052074 A1 * | 3/2003 | Chang et al. ................ 215/247 |
| 2003/0100111 A1 * | 5/2003 | Webb et al. ................. 435/455 |

FOREIGN PATENT DOCUMENTS

| | | |
|---|---|---|
| EP | 0 445 707 A2 | 3/1991 |
| EP | 0 454 493 A2 | 4/1991 |
| EP | 0 903 107 A1 | 8/1998 |
| EP | 1 155 742 A2 | 11/2001 |
| JP | 10-201742 | 8/1998 |
| WO | WO 89/02399 | 3/1989 |
| WO | WO 01/30490 A1 | 5/2001 |

* cited by examiner

*Primary Examiner*—Natalia Levkovich
(74) *Attorney, Agent, or Firm*—Hoffmann & Baron, LLP

(57) ABSTRACT

The present invention is a closed system storage plate that includes a specimen collection plate having a plurality of wells for storing specimens and a cover that is sealably secured to the specimen collection plate. The cover has a thermoplastic elastomer membrane that provides pierceable access by a probe to each well interior and self-seals upon removal of the probe.

22 Claims, 4 Drawing Sheets

CLOSED SYSTEM STORAGE PLATES

CROSS-REFERENCE TO RELATED APPLICATION

This claims the benefit of U.S. Provisional Patent Application No. 60/324,815, filed Sep. 25, 2001.

BACKGROUND OF THE INVENTION

1. Field of the Invention

The present invention relates to closed system storage plates that are used for the storage of specimens. More particularly, the invention relates to closed system storage plates that include a multi-well specimen collection plate and a cover suitable for storing a plurality of small quantities of specimens such as blood from a patient. The closed system storage plates provide access to the interior of each well without the need for removing the cover from the multi-well collection plate and maintains each specimen in secure fashion for subsequent testing.

2. Description of Related Art

Analytical instrumentation has made it possible to carry out a variety of hematological diagnostic procedures on very small quantities of blood. The blood may be collected from a small puncture placed in a patient's finger or ear lobe. When multiple specimens are collected, a microplate with a plurality of wells is used and the specimens are placed in the wells for subsequent analysis and testing. Typically, the microplate has a common cover for all of the microplate wells.

The growth in medical and pharmaceutical research as well as diagnostic analysis and testing has created a need for equipment and procedures for low cost, efficient handing of samples. Microplates having a plurality of sample wells provide a convenient means to store samples. However, despite improvements in sample handling equipment, many applications require an unacceptable amount of manual handling to cover or uncover the samples. In order for a laboratory technician to conduct tests on the blood samples which are collected in a microplate, the cover must be removed from all of the wells to provide access to the blood samples. When the laboratory technician tests a large number of wells, spillage and contamination of the samples becomes more likely. As a result, testing takes longer and the technician must proceed with greater care.

Mat caps have been used for storing multiple specimens. Typically, mat caps are thin films with adhesive coating and thin materials such as a plastic sheet that can be heat sealed to storage plates. The mat caps are fabricated from a pliable material that seals the plate by dimensional interference. However, mat caps and similar products require the cover to be removed for content access. Some mat caps are advertised to be pierceable, but none are resealable. Other methods for specimen storage include attaching thin films with adhesive coatings or other thin materials to the top of storage plates. Although these storage assemblies are pierceable, they cannot be resealed after they have been pierced.

To access a specific sample with the current mat cap designs, it is necessary to uncover all adjacent wells containing samples as well as the specific target well. Under these circumstances, all well contents are exposed to the environmental surroundings that can affect sample evaporation. Uncovering the samples also exposes the sample to ambient moisture, which can compromise the sample integrity. The possibility of contaminating samples in adjacent wells due to spillage or aerosols is also a concern.

Therefore, there is a need for a multi-well specimen storage plate that (i) independently seals each of the wells; (ii) provides a resealable well cover for easy access into each well by a needle or probe and also prevents specimen leakage out of the well; (iii) maintains the specimens in secure fashion; and (iv) prevents contamination of the specimens and exposure of the specimen to the user.

SUMMARY OF THE INVENTION

The present invention is a closed system storage plate that includes a specimen collection plate and a cover that is securely sealed to the plate. The specimen collection plate has a plurality of wells, wherein each well has an open end, a closed end and a cylindrical wall therebetween defining a well interior for accommodating a plurality of specimens. The cover is sealably secured to the specimen collection plate and sealably contacts the plurality of wells at the open end of each well. The cover includes a membrane for providing therethrough pierceable probe access to each well interior. The membrane is made of a thermoplastic elastomer and is self-sealing upon removal of the probe. The preferred elastomer material is isoprene propylene.

The specimen collection plate is made of plastic or borosilicate glass and the plurality of wells is made of borosilicate glass. In one embodiment, the open end of each well forms a flange that is sealably contacted by the cover. The cover can include an adhesive material that fixedly attaches the cover to the specimen collection plate and/or the flanges.

In a preferred embodiment, the cover for the closed system storage plate includes a plurality of membranes for providing therethrough pierceable probe access to each well interior. The location of the plurality of membranes corresponds to the location of the plurality of wells when the cover is sealably secured to the collection plate. The membranes are made of a thermoplastic elastomer and are self-sealing upon removal of the probe. The elastomer is preferably isoprene propylene, but other materials such as rubber can be used. The cover can include an adhesive material that contacts the specimen collection plate to fixedly attach the cover to the specimen collection plate.

In another preferred embodiment, the open end of each well forms a flange that is sealably contacted by the cover. When the cover is sealably secured to the collection plate, the plurality of membranes are so located on the cover that the membranes are inside the circumference of the flanges. This provides pierceable probe access to each of the wells through the corresponding membrane. The areas of the cover outside the circumference of the flanges may be formed from a material other than an elastomer, such as plastic or glass, which provides structural strength to the cover. When an adhesive material is used, it securely seals the cover to the flanges.

The cover includes the membrane (or membranes) that provides resealable access to the interior of the wells. The membrane is formed of a material which is capable of being pierced and resealed on a repetitive basis with a needle, a probe or a similar type of instrument. Most preferably, the membrane is formed of a thermoplastic elastomer such as isoprene propylene.

When the cover includes a plurality of membranes, the membranes are preferably disc-shaped and have a concave surface facing away from the well interior. This concave configuration assists in resealing the membrane after a probe has been withdrawn. In addition, the thermoplastic elastomer reseals the pierced membrane in a manner which prevents specimen leakage therethrough even when the collection assembly is held in an inverted position.

An advantage of the present invention is that it facilitates direct access to a sample in a microplate for diagnostic instrumentation systems and provides a pierceable and self-resealing cover.

Most notably, the present invention permits a specimen to be accessed through the cover without removing the cover from the specimen collection plate, thereby providing minimal exposure of the specimen to the user. Moreover, specimen quality is better maintained since each well is independently sealed and accessed and the cover reseals itself after puncture.

The closed system storage plates of the present invention provide several advantages by using a membrane that: (i) can be pierced and resealed many times; (ii) requires less than 2 lb. force for a piercing element to pierce it; and (iii) has a concave shape which assists in resealing the membrane after the piercing element is removed.

DETAILED DESCRIPTION

Figure 1:
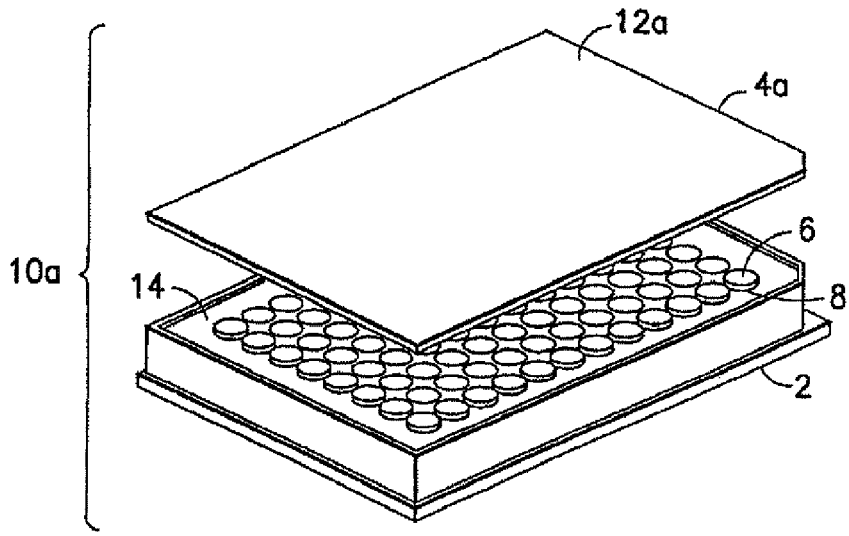
FIG. 1 is a perspective view of a closed system storage plate of the present invention showing the specimen collection plate and cover assembly.

The present invention is a closed system storage plate that includes a specimen collection plate having a plurality of wells arranged in a geometrical pattern and a cover that is securely sealed to it. Each well includes an open end, a closed end and a cylindrical wall therebetween that defines the interior of the well. The cover includes a thermoplastic elastomer material, which is capable of being pierced and self-resealing on a repetitive basis upon removal of the piercing device such as a pipette, cannula, or an instrument probe. The closed system storage plates permit specimens in each well to be dispensed or accessed without removing the cover from the specimen collection plate.

Direct access to the specimens through the cover and without the need to remove the cover from the plate provides minimal aerosol/airborne contaminant exposure to the user. With the current mat caps, there is an unnecessary risk to the user and work environment as a result of aerosols that can be created when removing the mat caps from wells containing specimens. In contrast, the closed system storage plates of the present invention maintain specimens, compounds, reagents, and the like in a secure and isolated fashion for subsequent dispensing, retrieving and storing.

The present invention is a closed storage system that includes a multi-well storage plate, and a non-removable cover. The plate is comprised of a plurality of wells, typically 96 or a 384 multi-well plate format, but storage plates with any number of wells can be used. The cover is hermetically sealed to provide a secure seal to the open end of each of the well structures of the plate and provides sealable access to the interior of the wells. The cover is fabricated from a thermoplastic elastomer material, which is capable of being pierced, and self-resealing on a repetitive basis upon removal of the piercing element such as a pipet tip, cannula, or an instrument probe.

The cover is substantially flat and includes a membrane that provides resealable access to the interior of the container. The membrane may extend across the entire cover or a plurality of membranes may be located selectively on the cover corresponding to the locations of the wells. The membrane is formed of a material that is capable of resealing after being pierced with a needle or instrument probe on a repetitive basis. Most preferably, the membrane is formed of a thermoplastic elastomer or a soft rubber. A preferred thermoplastic elastomer is an isoprene propylene, such as MONOPRENE (a trademark of QST, Inc.) sold by QST, Inc., St. Albans, Vt. Using molding techniques, such as insert molding and co-injection molding, the membrane can be incorporated into the cover in any location to provide access into the well.

In embodiments employing a plurality of membranes, the membranes may have a concave surface facing in opposition to the probe as it is withdrawn. The compressive forces exerted by the concave surface assist in resealing holes in the membrane as the probe is withdrawn from the well. Thus, the configuration of the membrane as well as the material from which it is formed permits the membrane to reseal after multiple punctures have been placed therein. The liquid sample in the wells can therefore be repeatedly sampled with the membrane self-sealing upon each sample extraction.

For the embodiments wherein the cover has a plurality of membranes, the cover includes a structure that supports the membranes. The structure may be made of metal, composites, glass or a plastic material such as polyethylene, polypropylene or polyvinyl chloride. Preferably, the cover material is compatible with organic solvents. The surface of the cover that contacts the multi-well plate may also include an adhesive. The adhesive can be either in the form of a layer or it can be selectively applied to the areas where the cover contacts the specimen collection plate.

Figure 2:
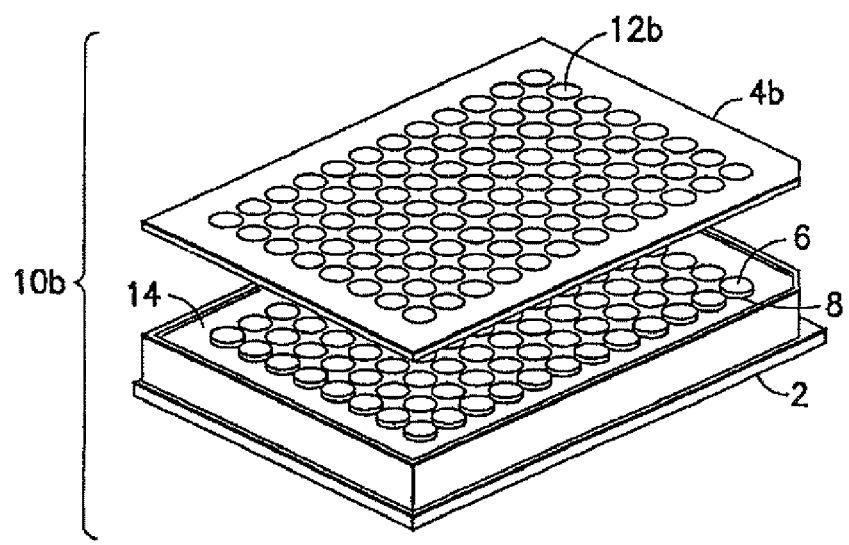
FIG. 2 is a perspective view of a closed system storage plate of the present invention showing the specimen collection plate and cover assembly with a plurality of membranes corresponding to the plurality of wells.
Figure 3:
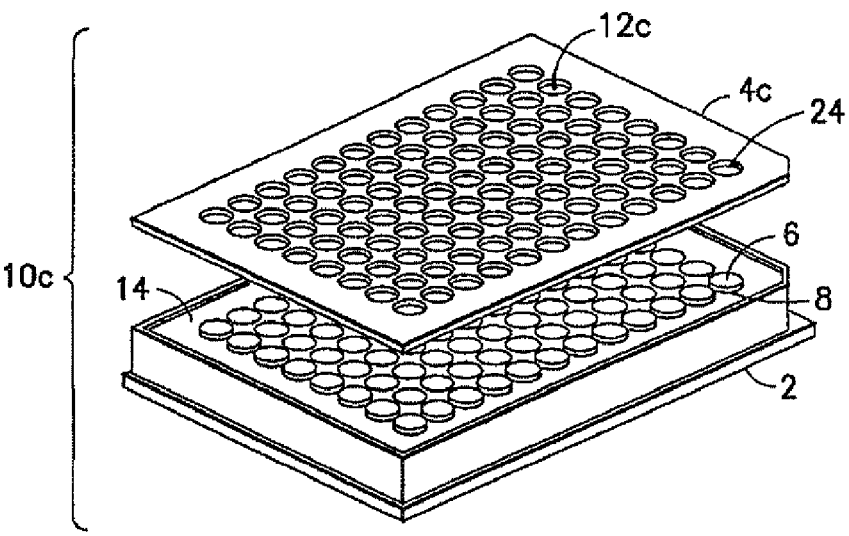
FIG. 3 is a perspective view of a closed system storage plate of the present invention showing the specimen collection plate and cover assembly with a plurality of skirted membranes corresponding to the plurality of wells.
Figure 10:
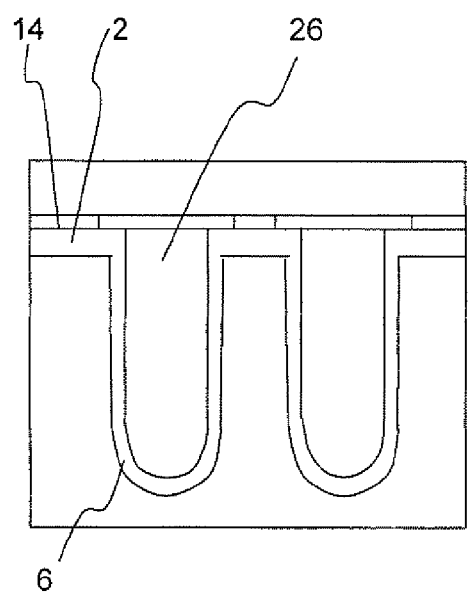
FIG. 10 shows the embodiment of FIG. 6 modified such that the wells are flush with the surface of the collection plate.

Referring to the drawings in which like reference characters refer to like parts throughout the several views thereof, FIGS. 1-3 illustrate three embodiments of the closed system storage plate 10a, 10b, 10c of the present invention. Each of the closed system storage plates 10a, 10b, 10c includes a specimen collection plate 2 and a cover 4a, 4b, 4c. The cover 4a, 4b, 4c may be removably or fixedly secured to the specimen collection plate 2. The specimen collection plate 2 includes a top surface 14 and a plurality of wells 6 arranged in a plurality of rows. Each well 6 forms a separate compartment that can be sealably isolated from the other wells 6 in the specimen collection plate 2. Each well 6 has an open upper end 26, a closed end 32 and a cylindrical wall 30 extending therebetween. The cylindrical wall 30 defines an interior 22 for accommodating a specimen such as a blood specimen. The open upper end 26 of the well 6 can be flush with the top surface 14 of the specimen collection plate 2 as shown for example in FIG. 10 or the cylindrical wall 30 can extend beyond the top surface 14 of the specimen collection plate 2 to form a peripheral lip or flange 8 as shown for example in FIG. 6.

The cover 4a, 4b, 4c is substantially planar and can be made in whole or in part of a pierceable and resealable membrane 12a, 12b, 12c for providing resealable access to the interior of each of the wells 6. The membrane 12a, 12b, 12c is preferably made of a thermoplastic elastomer material which is capable of being pierced and resealed on a repetitive basis with a needle or instrument probe. Most preferably, the membrane 12a, 12b, 12c is formed of a soft rubber or a thermoplastic elastomer, such as isoprene propylene.

FIG. 1 shows an embodiment of the present invention wherein the cover 4a is made of a thermoplastic elastomer and is sealably secured to the specimen collection plate 2 to isolate the plurality of wells 6. FIG. 2 shows a second embodiment wherein a plurality of membranes 12b made of a thermoplastic elastomer are located on the cover 4b while remainder of the cover 4b is made from a substantially rigid plastic. The plurality of membranes 12b correspond to the wells 6 and provides reseable access to the interior 22 of the individual wells 6. In a third embodiment shown in FIG. 3, each of the plurality of membranes 12c is enclosed by a skirt 24 that extends downwardly to sealably and circumferentially engage the interior or exterior of the cylindrical wall 30 of the well 6.

The specimen collection plate 2 has a plurality of wells 6 arranged in a geometric pattern. In the preferred embodiment, the geometric pattern is a rectangular array of 96 or 384 wells. However, in other embodiments, specimen collection plates 2 having different numbers of wells 6 or geometric patterns of wells are used. The specimen collection plate 2 is made of metal, composites, glass or a plastic material such as polyethylene or polypropylene. Stamping, die-casting or injection molding may be used to form the specimen collection plate 2. The depth of the wells 6 of the specimen collection plate 2 may vary according to the type and volume of the specimen. In preferred embodiments, the specimen collection plate 2 is made of a plastic material or glass and the wells 6 are made of glass. Glass wells 6 provide a material that is inert to most specimens and solvents. The preferred glass for both the specimen collection plate 2 and the wells 6 is borosilicate glass.

The open end 26 of the wells 6 may extend above the surface 14 of the specimen collection plate 2 to form a flange 8. When the cover 4a, 4b, 4c sealably contacts the specimen collection plate 2, the flange 8 ensures that the cover 4a, 4b, 4c impermeably seals each of the wells 6. In a preferred embodiment, a plurality of membranes 12b, 12c corresponding to the wells 6 is selectively located on the cover 4b, 4c so that when the cover 4b, 4c is sealably secured to the specimen collection plate 2, the membranes 12b, 12c provide access to each of the wells 6. The membranes 12b, 12c are located on the cover 4b, 4c within the circumference of the flanges 8.

The embodiment of the system storage plate 10a shown in FIG. 1 has a cover 4a that includes a substantially continuous layer of a thermoplastic elastomer that forms a membrane 12a. This allows a probe or other instrument to be inserted through the cover 4a at any point above the wells 6. In a preferred embodiment, the cover 4a also includes a structure 21 to support the thermoplastic elastomer membrane 12a and to provide rigidity. The structure 21 may include a frame around the perimeter of the cover 4a and/or ribs extending along the length and/or width of the cover 4a. The support structure 21 is preferably a hard plastic but other materials known in the art can be used. In another preferred embodiment, the cover 4a includes an adhesive 23 on the side of the cover 4a that contacts the specimen collection plate 2. The adhesive 23 can form a layer on the thermoplastic elastomer or it may be selectively applied to the cover 2a at the points that contact the specimen collection plate 2 and/or the wells 6.

The embodiment of the system storage plate 10b shown in FIG. 2 has a cover 4b which includes a plurality of membranes 12b that correspond to the locations of the wells 6 in the specimen collection plate 2. When the cover 4b is fixedly attached to the specimen collection plate 2, the membranes 12b are positioned above the wells 6 and provide pierceable access to the wells 6 through the membranes 12b. In a preferred embodiment, the non-membrane portions of the cover 4b may be made of a variety of materials known in the art, such as plastic, glass, composite materials or metal, preferably plastic or glass. An adhesive may be applied to the surface of the cover 4b that contacts the specimen collection plate 2 for sealably securing the cover 4b to the plate 2.

The embodiment of the system storage plate 10c shown in FIG. 3 has a cover 4c that includes a plurality of membranes 12c similar to the system storage plate 10b shown in FIG. 2. In addition to the plurality of membranes 12c, the cover 4c includes a plurality of skirts 14 extending downwardly from the surface of the cover 4c that contacts the specimen collection plate 2. These skirts 24 correspond to the wells 6 and extend into the interior or around the exterior of the wells 6 to provide a means for positioning the cover 4c so that the plurality of membranes 12c are located above the plurality of wells 6. In a preferred embodiment, the skirts 24 are made of plastic and are sealably secured to the cylindrical wall 30 of each well 6. In a most preferred embodiment, the skirts 24 are sealably secured to the well flanges 8.

Figure 4:
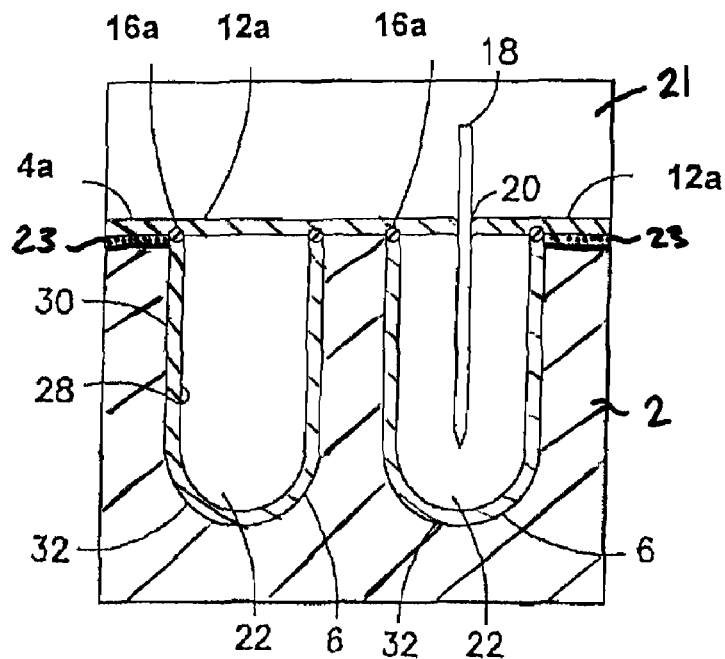
FIG. 4 is a side elevation view of two sealed wells, with one of the sealed wells having a probe extending thereinto.

FIG. 4 shows a preferred embodiment of the present invention, wherein the cover 4a is substantially flat and contacts the specimen collection plate 2 at the open end 26 of the wells 6 to form an impermeable seal 16a. A piercing element 18 such as a probe, cannula or pipet can be inserted through the cover 4a to access a specimen in the well 6. The probe 18 creates a temporary hole 20 in the membrane 12. After the probe 18 is withdrawn, the elastomer in the cover 4a reforms into an impermeable seal.

Figure 5:
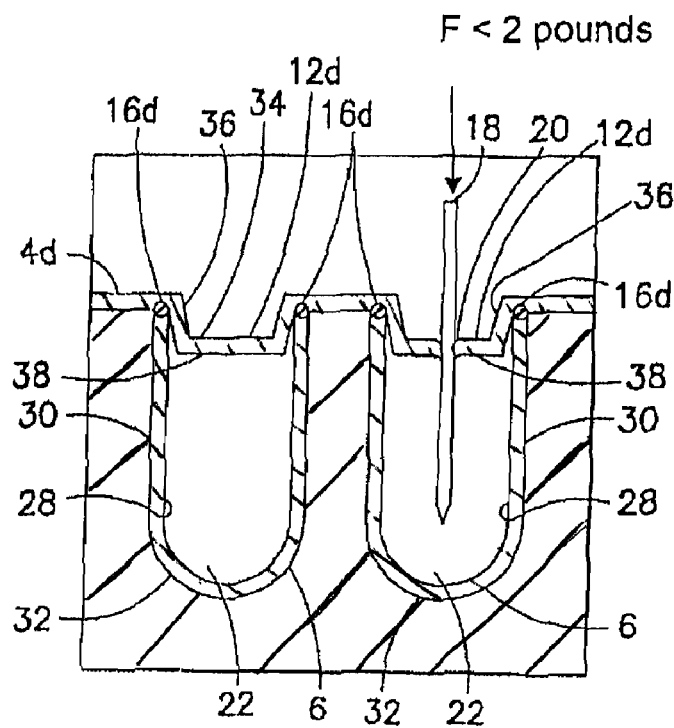
FIG. 5 is a side elevation view of two sealed wells with the membranes located in inverted caps and a probe extending into one of the wells.

FIG. 5 shows an embodiment of the present invention wherein the cover 4d includes a plurality of inverted caps 34 that correspond to the plurality of wells 6. Each cap 34 extends downwardly from the cover 4d and has an open top 36 a bottom 38 and a cylindrical side wall 40 that slopes inwardly from the open top 36 to the bottom 38. The caps 34 contact the interior walls 28 of the wells 6 to securely seal the interior 22 of the wells 6. The caps 34 are made of the same material as the cover 4d, preferably plastic. A membrane 12d is located at the bottom 38 of each cap 34 so that a probe 18 can pierceably access the specimen in the well 6. When the probe 18 is withdrawn from the membrane 12d, the thermoplastic elastomer in the membrane 12d reforms to seal the hole 20 in a manner that specimen leakage even when the storage assembly is inverted.

As shown in FIG. 4 and FIG. 5, a sample probe or cannula 18 may access a well 6 by inserting the probe 18 through membrane 12a, 12b, 12d. The probe 18 is inserted until it reaches the sample in interior 22 of well 6 and then collects a portion of the sample. The probe 18 is then removed by withdrawing it back through the membrane 12a, 12b, 12d. After the probe 18 is from the well 6, the thermoplastic elastomer at the insertion point 20 self-seals. Since the membrane 12a, 12b, 12d is made of a soft rubber or thermoplastic elastomer, a low insertion force easily pierces it. Therefore, for a relatively wide instrument probe 18 having a diameter of about 0.0625 inches, a force of less than 2 pounds can pierce the membrane 12a, 12b, 12d.

The closed system storage plate of the present invention may be made of a molded thermoplastic material so that the specimens collected in the wells may be readily viewed. Representative materials include, for example, polyethylene, polypropylene and polyvinyl chloride. The wells may incorporate a hydrophilic material or a silicon, or a texture may be applied to the internal surface thereof for enhancing the flow and mixing of blood introduced into the wells.

Although it is within the purview of the invention to provide closed system storage plates that are colored to define specific applications for the plates or to define the tests that are conducted on the specimens collected, transparent covers may be provided. Also, it should be noted that the dimensions of the closed system storage plate are such as to provide space for labeling which may be important for identifying the collected specimens.

As shown in FIG. 5, the force of less than 2 pounds is labeled "F".

Figure 6:
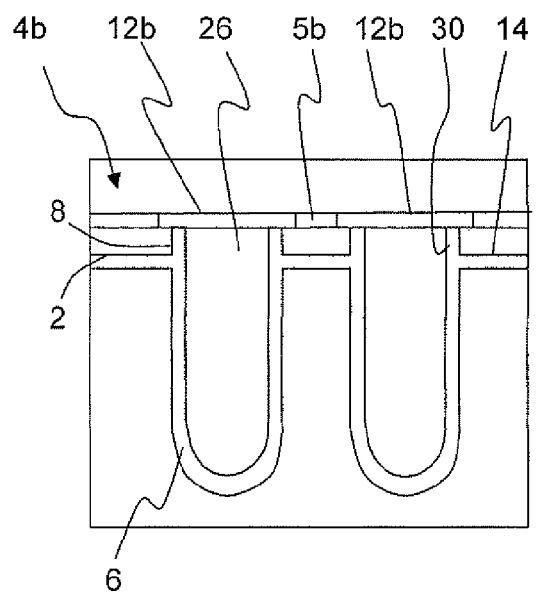
FIG. 6 shows the open end of a well extending above the surface of the collection plate to form a flange that is sealably contacted by a cover and shows the cover that is sealably secured to the specimen collection plate and sealably contacts the plurality of wells at the open end of each well, wherein the cover has a structure and a plurality of separate membranes supported on the structure and positioned respectively above the plurality of wells when the cover is fixedly attached to the specimen collection plate, the membranes being disc-shaped and providing therethrough pierceable probe access to each well interior, wherein the membranes are formed of a thermoplastic elastomer.

FIG. 6 shows an enlarged view of the embodiment of FIG. 2 wherein the open end 26 of a well 6 extends above the surface of the collection plate 2 to form a flange 8 that is sealably contacted by a cover 4b and shows the cover 4b sealably secured to the specimen collection plate 2 and sealably contacts the plurality of wells 6 at the open end 26 of each well, wherein the cover 4b has a structure 5b and a plurality of separate membranes 12b supported on the structure 5b and positioned respectively above the plurality of wells 6 when the cover 4b is fixedly attached to the specimen collection plate 2, the membranes 12b being disc-shaped and providing therethrough pierceable probe access to each well interior, wherein the membranes 12b are formed of a thermoplastic elastomer.

Figure 7:
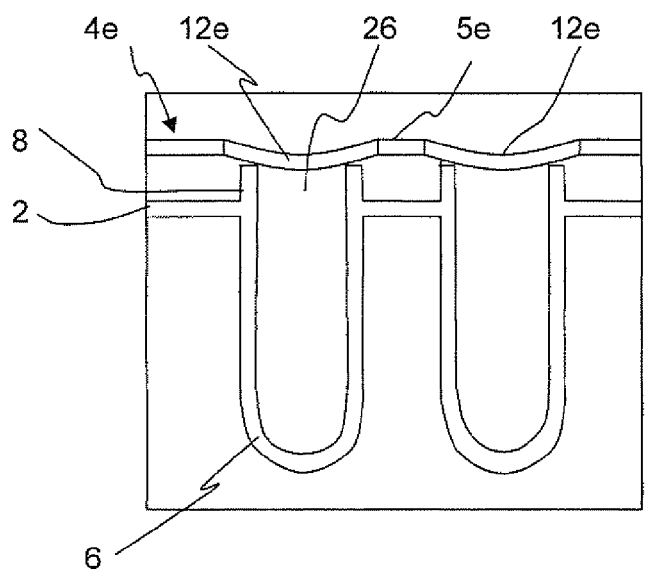
FIG. 7 shows the embodiment of FIG. 6 wherein the membranes are modified to be disc-shaped and have a concave surface facing away from the well interior.

FIG. 7 shows the embodiment of FIG. 6 having a cover 4d that is sealably secured to the specimen collection plate 2 and sealably contacts the plurality of wells 6 at the open end 26 of each well 6, wherein the cover 4d has a structure 5e and a plurality of separate membranes 12e supported on the structure 5e and positioned respectively above the plurality of wells 6 when the cover 4e is fixedly attached to the specimen collection plate 2, the membranes 12e providing therethrough pierceable probe access to each well interior, wherein the membranes 12e are formed of a thermoplastic elastomer, wherein the membranes 12e are modified to be disc-shaped and have a concave surface facing away from the well interior.

Figure 8:
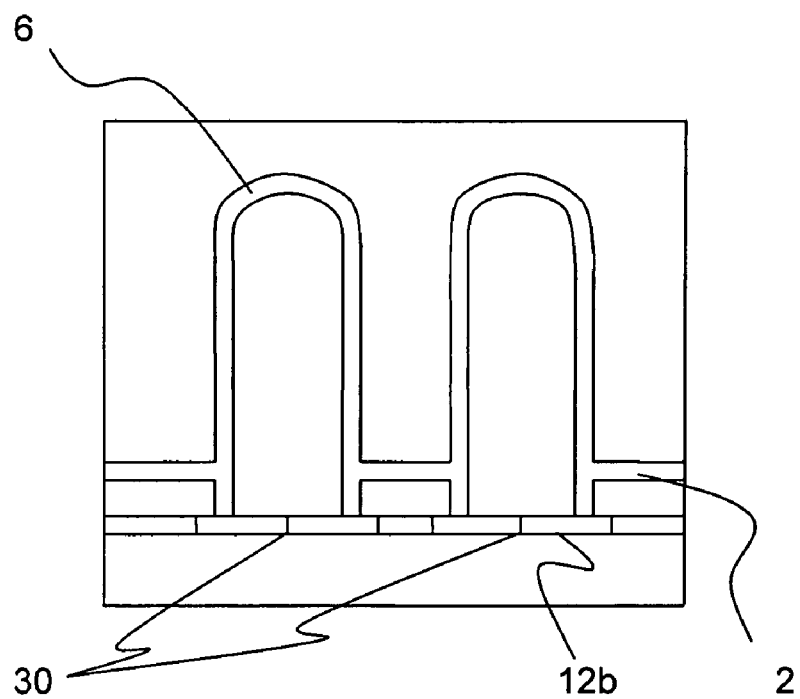
FIG. 8 shows the embodiment of FIG. 6 after piercing while held in an inverted position and being sufficiently resealed to prevent specimen leakage when held in the inverted position.

FIG. 8 shows the embodiment of FIG. 6 after piercing while held in an inverted position and being sufficiently resealed at a slit 30 of each well 6 formed by the probe 18 (not shown because now removed) to prevent specimen leakage when held in the inverted position.

Figure 9:
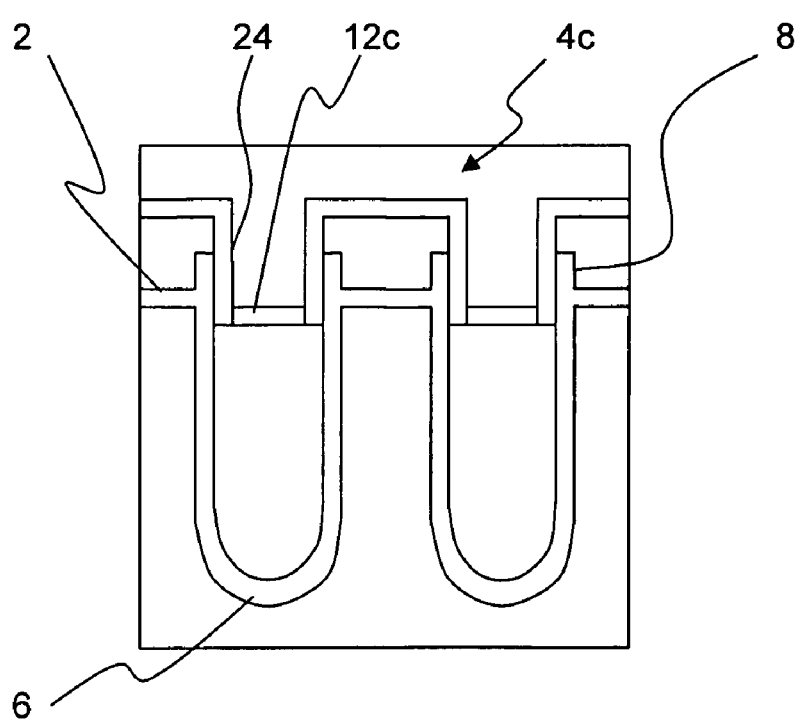
FIG. 9 shows an enlarged view of a portion of the embodiment of FIG. 3 to show a skirt holding the membrane and inserted into a respective well to contact the inner sidewalls of the respective well.

FIG. 9 shows an enlarged view of the embodiment of FIG. 3 to show the skirt 24 holding the membrane 12c and inserted into the respective well 6 to contact the inner sidewalls of the respective well 6.

Thus, while there have been described the preferred embodiments of the present invention, those skilled in the art will realize that other embodiments can be made without departing from the spirit of the invention, and it is intended to include all such further modifications and changes as come within the true scope of the claims set forth herein.

What is claimed is:

1. A closed system storage plate consisting of:
a specimen collection plate having a plurality of wells, wherein each well has an open end, a closed end and a cylindrical wall therebetween defining a well interior for accommodating a plurality of specimens, wherein said specimen collection plate comprises plastic and said plurality of wells comprise borosilicate glass; and
a cover that is sealably secured to said specimen collection plate and sealably contacts said plurality of wells at said open end of each well, said cover comprising a frame-shaped structure and a membrane for providing therethrough pierceable probe access to each said well interior, said frame-shaped structure supporting said membrane with portions of said membrane being exposed through said frame-shaped structure, wherein said cover, when disposed on said specimen collection plate over, and between, said wells, sealably isolates said wells from each other at the interface of said cover and specimen collection plate with and without a probe piercing said membrane, said membrane being pierceable by the probe above said wells with said cover sealably isolating said wells from each other,
said membrane being formed of a thermoplastic elastomer and configured for resealing temporary holes made in the membrane from repeated sampling of each said well by the probe.

2. The closed system storage plate of claim 1, wherein said open end of each well extends above the surface of the collection plate to form a flange that is sealably contacted by said cover.

3. The closed system storage plate of claim 1, wherein said elastomer is isoprene propylene.

4. The closed system storage plate of claim 1, wherein said cover further comprises an adhesive material.

5. The closed system storage plate of claim 4, wherein said cover and said specimen collection plate are fixedly attached by said adhesive material.

6. The closed system storage plate of claim 1, wherein said open end of each well extends above the surface of the collection plate to form a flange that is sealably contacted by said cover.

7. A closed system storage plate consisting of:
a specimen collection plate having a plurality of wells, wherein each well has an open end, a closed end and a cylindrical wall therebetween defining a well interior for accommodating a plurality of specimens, wherein said specimen collection plate comprises plastic and said plurality of wells comprise borosilicate glass; and
a cover sealably secured to said specimen collection plate and sealably contacts said plurality of wells at said open end of each well, said cover comprising a rigid structure and a plurality of separate membranes supported on said structure and positioned respectively above the plurality of wells when the cover is fixedly attached to the specimen collection plate, said membranes providing therethrough pierceable probe access to each said well interior, said membranes being formed of a thermoplastic elastomer;

wherein each membrane of said plurality of membranes being formed of a thermoplastic elastomer and configured for providing compressive forces for assisting in resealing a first temporary hole formed in the membrane by the probe upon removal of the probe and assisting in resealing multiple additional temporary holes made in the membrane from repeated sampling of each said well by the probe.

8. The closed system storage plate of claim 7, wherein said plurality of membranes corresponds to said plurality of wells.

9. The closed system storage plate of claim 7, wherein said open end of each well extends above the surface of the collection plate to form a flange that is sealably contacted by said cover.

10. The closed system storage plate of claim 7, wherein said elastomer is isoprene propylene.

11. The closed system storage plate of claim 7, wherein said cover further comprises an adhesive material.

12. The closed system storage plate of claim 11, wherein said cover and said specimen collection plate are fixedly attached.

13. The closed system storage plate of claim 7, wherein said membranes are disc-shaped and have a concave surface facing away from the well interior.

14. The closed system storage plate of claim 1, wherein said membrane is formed and configured to prevent specimen leakage therethrough when the specimen collection plate is in an inverted position.

15. The closed system storage plate of claim 1, wherein said membrane requires less than two pounds force to be applied to the probe to be pierced.

16. The closed system storage plate of claim 7, wherein each of the membranes contacts the open end of a respective said well.

17. The closed system storage plate of claim 1, wherein said open end of each well is flush with the surface of the collection plate.

18. The closed system storage plate of claim 7, wherein said open end of each well is flush with the surface of the collection plate.

19. A closed system storage plate consisting of:
a specimen collection plate having a plurality of wells, wherein each well has an open end, a closed end and a cylindrical wall therebetween defining a well interior for accommodating a plurality of specimens, wherein said specimen collection plate comprises plastic and said plurality of wells comprise borosilicate glass; and
a cover sealably secured to said specimen collection plate and sealably contacts said plurality of wells at said open end of each well, said cover comprising a membrane for providing therethrough pierceable probe access to each said well interior,
said membrane being formed of a thermoplastic elastomer and configured for providing compressive forces for assisting in resealing a first temporary hole formed in the membrane by the probe upon removal of the probe and assisting in resealing multiple additional temporary holes made in the membrane from repeated of each said well by the probe,
wherein the cover includes a plurality of inverted caps that correspond to the plurality of wells, wherein each cap extends downwardly from the cover into the respective well and has an open top, a bottom wall, and a frustoconical side wall that slopes inwardly from the open top to the bottom, the caps contact interior walls of the wells, respectively, a respective portion of said membrane is located at a respective said bottom wall of the cap.

20. A closed system storage plate consisting of:
a specimen collection plate having a plurality of wells, wherein each well has an open end, a closed end and a cylindrical wall therebetween defining a well interior for accommodating a plurality of specimens, wherein said specimen collection plate comprises plastic and said plurality of wells comprise borosilicate glass; and
a cover sealably secured to said specimen collection plate and sealably contacts said plurality of wells at said open end of each well, said cover comprising a structure and a plurality of separate membranes supported on said structure and positioned respectively above the plurality of wells when the cover is fixedly attached to the specimen collection plate, said membranes providing therethrough pierceable probe access to each said well interior, said membranes being formed of a thermoplastic elastomer;
wherein each membrane of said plurality of membranes being formed of a thermoplastic elastomer and configured for providing compressive forces for assisting in resealing a first temporary hole formed in the membrane by the probe upon removal of the probe and assisting in resealing multiple additional temporary holes made in the membrane from repeated sampling of each of said well by the probe,
wherein the cover includes a plurality of inverted caps that correspond to the plurality of wells, wherein each cap extends downwardly from the cover into the respective well and has an open top, a bottom wall, and a frustoconcial side wall that slopes inwardly from the open top to the bottom, the caps contact interior walls of the wells, respectively, and a said membrane of said plurality of separate membranes is located at a respective said bottom wall of the cap.

21. The closed system storage plate of claim 2, wherein each said well cylindrical wall extends from the open end to the closed end and has a constant inner diameter.

22. The closed system storage plate of claim 9, wherein each said well cylindrical wall extends from the open end to the closed end and has a constant inner diameter.

* * * * *